US006783539B1

(12) United States Patent
Timberlake et al.

(10) Patent No.: US 6,783,539 B1
(45) Date of Patent: Aug. 31, 2004

(54) PHOTOTRIGGERABLE, COLLAGEN-CROSSLINKING COMPOUNDS FOR WOUND CLOSURE

(75) Inventors: George T. Timberlake, Overland Park, KS (US); Richard S. Givens, Lawrence, KS (US); Peter G. Conrad, II, Irvine, CA (US)

(73) Assignee: University of Kansas Medical Center, Kansas City, KS (US)

( * ) Notice: Subject to any disclaimer, the term of this patent is extended or adjusted under 35 U.S.C. 154(b) by 0 days.

(21) Appl. No.: 10/113,426

(22) Filed: Mar. 29, 2002

Related U.S. Application Data
(60) Provisional application No. 60/280,165, filed on Mar. 30, 2001.

(51) Int. Cl.[7] .................. A61B 17/03; C07C 245/12; C07K 14/78
(52) U.S. Cl. .................. 606/214; 156/272.2; 525/54.1; 530/356; 534/561; 534/564; 604/20
(58) Field of Search .................. 606/2, 3, 4, 214; 534/561, 564; 156/272.2, 275.3, 275.7; 604/20, 290, 500, 521; 525/54.1; 530/300, 345, 356; 514/2, 8, 21; 424/78.17, 78.27

(56) References Cited

U.S. PATENT DOCUMENTS

| 5,917,045 A | 6/1999 | Lewis et al. ................ 546/100 |
| 6,410,505 B1 | 6/2002 | Lewis et al. .................. 514/63 |

OTHER PUBLICATIONS

Chemical Abstracts, vol. 124, No. 25, Abstract No. 124:342624w (Jun. 17, 1996).*
Goodfellow et al. p–Nitrophenyl 3–Diazopyruvate and Diazopyruvamides. . . Biochemistry. 1989, vol. 28, pp. 6346–6360.*

Judy, Millard M., Jackson, R.W., Nosir, Hany R., Matthews, J.L., Loyd, John D., Lewis, David E., Utecht, Ronald E., Yuan, Dongwu. Healing results in meniscus and articular cartilage photochemically welded with 1,8–naphthalimide dyes. Proceedings of SPIE. Lasers in Surgery: Advanced Characterization, Therapeutics, and Systems VII. (1997). 2970:257–260.

Judy, Millard M., Jackson, R.W., Nosir, Hany R., Matthews, J.L., Lewis, David E., Utecht, Ronald E., Yuan, Dongwu. Repair of articular cartilage and meniscal tears by photoactive dyes: In vivo study. Proceedings of SPIE. Laser Applications in Medicine and Dentistry. (1996). 2922:436–440.

Judy, Millard M., Nosir, Hany R., Jackson, R.W., Matthews, J.L., Lewis, David E., Utecht, Ronald E., Yuan, Dongwu. Bonding of human meniscal and articular cartilage with photoactive 1,8–naphthalimide dyes. Proceedings of SPIE. Lasers in Surgery: Advanced Characterization, Therapeutics, and Systems VI. (1996). 2671:251–255.

Judy, Millard M., Fuh, L., Matthews, J.L., Lewis, David E., Utecht, R. Gel eletrophoretic studies of photochemical cross–linking of Type I collagen with brominated 1,8–naphthalimide dyes and visible light. Proceedings of SPIE. (1994). 2128:506–509.

Judy, Millard M., Matthews, J.L., Boriack, R.L., Burlacu, A. Photochemical cross–linking of proteins with visible–light–absorbing 1,8–naphthalimides. Proceedings of SPIE. Laser–Tissue Interaction IV. (1993). 1882:305–308.

(List continued on next page.)

Primary Examiner—Jeffrey Edwin Russel
(74) Attorney, Agent, or Firm—Stinson Morrison Hecker LLP

(57) ABSTRACT

A phototriggerable composition and method for use in crosslinking protein such as collagen comprising application of a tethered diazopyruvate composition followed by irradiation, whereby the composition results in the sutureless wound closure of, for example, a tendon or cornea.

5 Claims, 3 Drawing Sheets

OTHER PUBLICATIONS

Judy, Millard M., Matthews, J.L., Boriack, R.L., Burlacu, A., Lewis, David E., Utecht, Ronald E. Heat–free photochemical tissue welding with 1,8–naphthalimide dyes using visible (420 nm) light. Proceedings of SPIE. (1993). 1876:175–179.

Kloster, Kaia L., Judy, Millard M., Matthews, James L., Utecht, Ronald E., Burbach, James A., Vaska, Kevin J. Preferential Localization of Varying Forms of Photoactive 1,8–Naphthalimide Compounds Within the Atheromatous Arterial Wall. Lasers in Surgery and Medicine (2000). 26:316–322.

Judy, Millard M., Nosir, Hany R., Jackson, R.W., Matthews, J.L., Utecht, Ronald E., Lewis, David E., Yuan, Dongwu. Photochemical bonding of skin with 1,8–naphthalimide dyes. Proceedings of SPIE. (1997). 3195:21–24.

Judy, Millard M., Chen, L., Fuh L., Nosir, H., Jackson, R.W., Matthews, J.L., Lewis, D.E., Utecht, R.E., Yuan, D. Photochemical cross–linking of type I collagen with hydrophobic and hydrophilic 1,8 naphthalimide dyes. Proceedings of SPIE. (1996). 2681:53–55.

Chang, Shao–Chieh, Archer, Bradley J., Utecht, Ronald E., Lewis, David E., Judy, Millard M., Matthews, James L. 4–Alkylamino–3–Bromo–N–Alkyl–1,8–Naphthalimides; New Photochemically Activatble Antiviral Compounds. Bioorganic & Medicinal Chemistry Letters. (1993). 3:555–556.

* cited by examiner

PHOTOTRIGGERABLE, COLLAGEN-CROSSLINKING COMPOUNDS FOR WOUND CLOSURE

CROSS-REFERENCE TO RELATED APPLICATIONS

This application claims the benefit of U.S. Provisional Application Serial No. 60/280,165, filed on Mar. 30, 2001, which is hereby incorporated by reference.

STATEMENT REGARDING FEDERALLY SPONSORED RESEARCH OR DEVELOPMENT

Not Applicable.

FIELD OF THE INVENTION

The present invention relates to a phototriggerable composition and method for use in crosslinking protein. More specifically, the present invention relates to a tethered diazopyruvate composition for use in crosslinking collagen, whereby the composition results in sutureless wound closure, for example, of a tendon or cornea.

BACKGROUND OF THE INVENTION

There is a desire to replace sutures in ocular surgery with a light-activated collagen bonding agent. Elimination of sutures by use of such a bonding agent would be of benefit primarily in corneal procedures. The number of penetrating keratoplasties performed in the United States is steadily increasing, with more than 30,000 being performed in 1994. Overall, penetrating keratoplasty is a highly successful procedure with reported graft survival rates of 79% to 90% after 3–5 years. Although thousands of successful corneal transplants are performed each year, there are significant drawbacks to the present surgical procedure. The major problem is that opposed stroma of the donor and recipient corneas do not fully and uniformly rejoin. Rather, sporadic fibrous scar tissue is formed at different locations along the wound by activated keratocytes as part of the corneal wound healing process. The fibrous tissue crosses from one side of the incision to the other, but the original lamellar structure is never reestablished. Furthermore, the degree of fibrous interconnection can vary from one area of the incision to another so that when the sutures are removed, there may be localized wound gaping and consequent astigmatism. The lack of fully rejoined collagen results in a weakened corneal structure, and consequently, blows to the cornea can result in wound dehiscence and severe ocular damage. Although wound dehiscence is not the major cause of graft failure, it poses a significant problem. For example, it has been reported that about 4% of wound failures are due to wound dehiscence and leakage.

A second major problem with the present surgical method concerns the sutures themselves. First, the suture material can initiate an inflammatory response with resulting pain, irritation, and invitation of blood vessels. Second, suturing makes a hole in the cornea that allows entry of infectious agents that are normally excluded by the epithelium. Third, sutures do not apply even pressure along the circumference of the wound. Areas of the wound that are not firmly held together are susceptible to leakage of aqueous humor and epithelial downgrowth. Together, the problems of inflammation, irritation, wound gape, leakage and epithelial downgrowth pose significant clinical problems in postsurgical management of corneal transplant and are frequent causes for transplant failure. It is known that the most common complications after graft placement are related to the sutures. In fact, it has been observed that 25% of patients experience suture complications including exposed sutures, stitch abscess, breakage and loosening, and wound dehiscence.

Sutures are also a frequent cause of post-operative visits to emergency rooms. For example, it has been observed that 14.4% of patients with corneal or conjunctival monofilament nylon sutures make two or more extra visits to the emergency room due to ocular irritation caused by loosened or broken sutures. For these reasons, it is desired to have a composition or method, which can be used in place of known surgical methods. Such method or composition will preferably eliminate the need for sutures.

It is further desired to be able to repair other types of collagenous tissue. Surgery on other bodily collagenous tissues may benefit from development of a phototriggerable collagen crosslinker. For example, tendon repair would seem an ideal candidate because, like the cornea, tendon is primarily Type I collagen, has little vascularization, and normally contains few active cells. Surgical repair of tendons occurs as a treatment for injury or as a corrective measure for patients with neurological deficits with accompanying abnormal tone, pulling an extremity into an undesirable position. The most commonly performed surgical procedures for stroke patients are: (1) tendon lengthening or release, (2) soft-tissue release, and (3) tendon transfers. Furthermore, tendons are the most prevalent site of surgery for the correction of overuse or chronic repetitive use problems (32% of all surgery relating to overuse is for tendons).

Tendon healing is a slow process, requiring at least six weeks, that may lead to extended hospitalization times with prolonged inactivity resulting in long-lasting morbidity. Human studies have shown that six months following surgery, the Achilles tendon has not recovered concentric or eccentric plantar flexion muscle strength compared to non-injured tendons. Following ligament-tendon autografts, low mechanical strength has been reported in the tendons of various animal models as long as one to three years after surgery. In addition, it has been found, using a rabbit, Achilles tendon model, that two weeks following reapproximation with sutures, tendons have less than half the strength of intact tendons and the decreased strength remains for at least 6 months. Clinically, prolonged healing of sutured tendons requires long periods of immobilization, predisposing patients to muscle atrophy, joint cartilage ulceration, tendo-cutaneous adhesion, and rerupture. What is desired is a composition that improves the tendon healing because it would provide immediate collagen-to-collagen bonds that otherwise are only re-established through the long-term wound healing mechanism when sutures alone are used for repair. It is especially desired to have a composition that eliminates the need for sutures.

For phototriggerable, collagen-crosslinking compounds to be useful in surgical wound closure, light of the appropriate wavelength must penetrate the tissue deeply enough to activate all of the material while not damaging the tissue. Previously developed phototriggerable compounds are activated in the 250 nanometer (nm) to 350 nm range, a spectral range potentially damaging to the eye. Therefore, an important design criterion is to select chromophores that can be activated at wavelengths that produce sufficient penetration with minimal phototoxicity. For the eye, this wavelength range is approximately 330 nm to 400 nm since absorption by cornea is quite low, and phototoxic effects are minimal. Thus, by proper selection of the chromophore, it is possible to design and synthesize phototriggerable compounds that are activated at wavelengths that will penetrate collagenous tissues deeply, yet cause minimal phototoxic effects.

The intact cornea is approximately 78% water by weight, hence phototriggerable crosslinkers must readily penetrate the aqueous environment of the tissue in order to form bonds with collagen. Tendon, sclera, and conjunctiva also have relatively high water contents. Consequently, an important design consideration for phototriggerable crosslinkers is to make them hydrophilic.

Previous experience with 1,8-naphthalimide dye suggests that this compound is extremely quantum inefficient; that is, the number of chemical bonds formed per incident photon is quite low. This, in turn, necessitates extremely high total energies to form tissue bonds, which is problematic for realistic surgical application. Thus, a suitable phototriggerable crosslinker, should have a relatively high quantum efficiency.

BRIEF SUMMARY OF THE INVENTION

The present invention relates to a photoactivated composition for crosslinking protein wherein the composition is a diazopyruvate of the general formula $RHNCOCOCHN_2$ where R is selected preferably from the group consisting of oligopeptides and polyethylene glycol. Generally, the composition is described as a tethered photoactivated compound having two diazopyruvate molecules. The preferred composition to be photoactivated is an N,N'-bis(3-diazopyruvoyl)-2,2'-(ethylenedioxy)bis(ethylamine) that is in a solution and can be applied to the tissue. The crosslinked protein is, more specifically, a collagen composition. Activation of the photoactive composition occurs at a wavelength that is non-damaging to the surrounding tissue. Suitable wavelengths range between 330 nm and 400 nm. Preferably, the composition is hydrophilic and non-toxic. The composition used to tether the photoactive compound is selected from the group consisting of polyethylene glycol and oligopeptides.

The present invention also relates to a method for crosslinking proteins. The method includes: forming a hydrophilic, non-toxic photoactive composition; applying the composition to collagenous tissue; and, irradiating such composition at a wavelength of between 300 nm and 400 nm, whereby the tissue wound is repaired. Irradiation forms a reactive intermediate composition that forms covalent bonds with the collagen. The intermediate is a ketoketene and will bond with the free amine of an amino acid such as lysine. The resultant crosslinked composition is typically a bis-1,n-malonylamide.

DETAILED DESCRIPTION OF THE INVENTION

Figure 1:
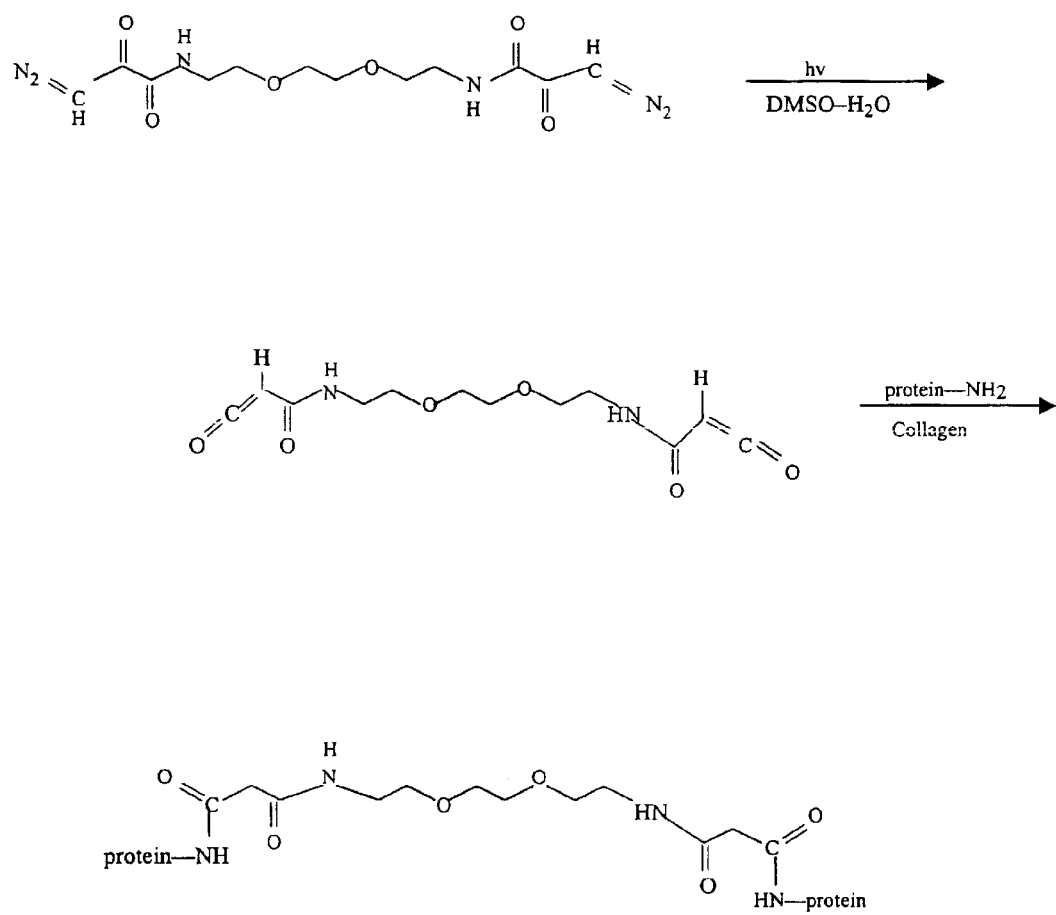
FIG. 1 is a reaction schematic showing two proteins crosslinked by a tethered diazopyruvate composition.

The present invention relates to a composition that is photoactivated for use in crosslinking protein, specifically collagen, whereby the composition can be used to close or weld cuts or tears of collagenous tissue, such as a tendon or cornea. The present invention also relates to methods for crosslinking proteins, methods for forming the photoactivated composition, and methods of application. The inventive composition also relates to a photoactivated intermediate that reacts with the free amine of an amino acid, such as lysine. The resulting crosslinked collagenous tissue, whereby the crosslinking compound is tethered and includes two photoactivated molecules, is part of the present inventive composition. The overall reaction is shown in FIG. 1.

Figure 5:
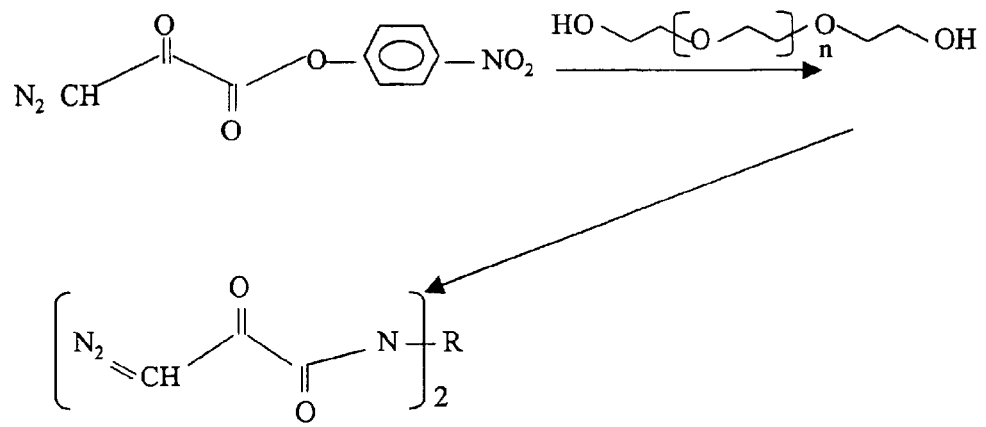
FIG. 5 illustrates the synthesis of a bifunctional diazopyruvate from 4-nitrophenyl-3 diazopyruvate reacted with a tethering composition; and, FIG. 6 illustrates the reaction of a diazapyruvate with an amine on a protein to form a tethered malonylamide.

The photoactivated composition is formed by tethering two photoactivated molecules, as shown in FIG. 5, where R is equal to the tethering compound. The photoactivated composition is formed by reacting two diazopyruvate compounds with a tethering composition. Preferably, the diazopyruvate is 4-nitrophenyl-3-diazopyruvate. The tether is typically either an oligopeptide or an ether chain. The resultant compound shown in FIG. 5 is the tethered diazopyruvate, with R equal to the tether.

Figure 3:
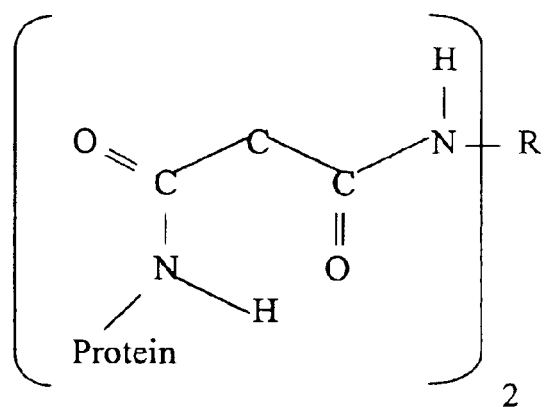
FIG. 3 is an illustration of a protein bonded to the diazopyruvate molecule, with R equal to a tether compound.
Figure 4:
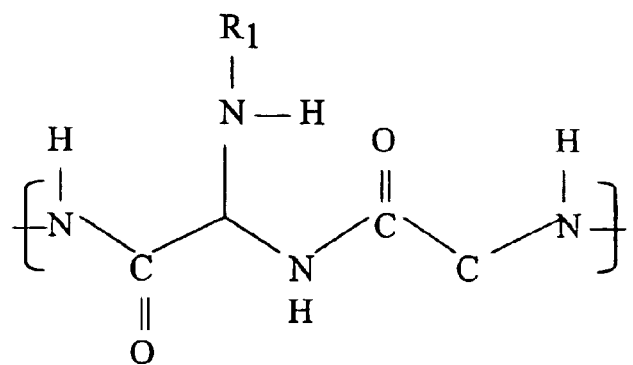
FIG. 4 is an illustration of an amino acid that can be bound to a photoactive composition, with $R_1$ equal to the photoactive compound.

Any of a variety of photoactivated molecules can be used as long as the molecule has the below-discussed characteristics. The molecules should be triggered at a wavelength ranging between 330 nm and 400 nm or any other wavelength that does not readily damage human tissue. This wavelength is preferred because it sufficiently penetrates the eye without causing significant damage thereto. The photoactivated molecules must be such that they can be tethered or connected to one another. If the photoactivated molecules are not tethered or linked to one another, then it is unlikely a wound or cut will be closed. When irradiated, the phototriggerable molecule must be activated such that it will form a covalent bond with part of a protein, in particular, an amino acid. Preferably, the amino acid that is bonded is lysine because of the prevalence of lysine in collagenous tissue. FIG. 4 illustrates a suitable amino acid structure for bonding with the present composition. Also, FIG. 3 shows the protein bonded to the diazopyruvate compound. Like before, R is equal to the tether compound. A high quantum absorption, meaning increased quantum efficiency, is preferred, as this results in an increase in the efficiency of binding to the protein.

Figure 2:
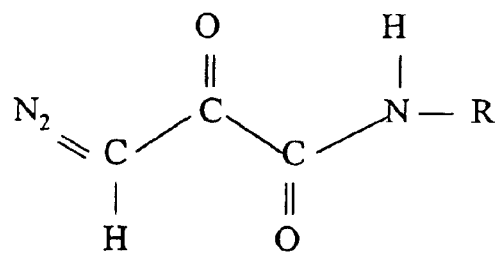
FIG. 2 is an illustration of a diazopyruvate molecule, with R equal to a tether compound.

The preferred photoactivated molecule for use in the present invention is a diazopyruvate. It is of the general formula $RHNCOCOCHN_2$ and is shown in FIG. 2, with R equal to the tether compounds. The photoactive molecules are preferably tethered or bound by an ether chain or an oligopeptide chain. The ether chain is comprised of ethylene glycol units, for example, polyethylene glycol (PEG). The oligopeptide chain is comprised of amino acid units. The oligopeptide will preferably have between 4 and 8 amino acid units.

Once formed, the photoactivated composition is mixed into a solution. The solution can be either a buffered saline solution or a dimethyl sulfoxide (DMSO). One mole of the photoactivated composition will be present in the solution. It is preferred for the photoactivated composition to be hydrophilic. The solution containing the photoactivated composition is applied to the tissue structure to be repaired. Once the composition is applied to the tissue, it is activated at a wavelength ranging between 330 nm and 400 nm to cause formation or an activated intermediate. Irradiation typically occurs for between 2 and 10 minutes.

Figure 6:
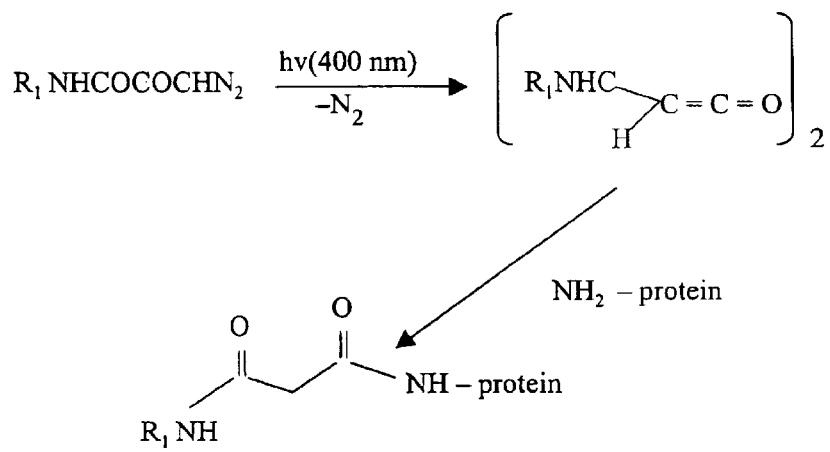

The activated intermediate is preferably a ketoketene. The ketoketene is shown in FIGS. 1 and 6, and readily reacts with the amine group of a protein, in particular, lysine. In FIG. 6, $R_1$ is the tether composition. When irradiated, the photoactivated diazopyruvate undergoes an Arndt-Eisert rearrangement to the highly reactive bis-1,N ketoketene. The reactive ketoketene forms a crosslink with lysine to form a crosslinked protein, which is a tethered malonylamide. A covalent bond is formed which readily closes the cut of the cornea tissue or the tendon. The resulting wound closure is stronger than traditional sutures.

EXAMPLES

Example 1

A mixture of 1.2 M of DPD N,N'-bis(3-diazapynivoyl)-2,2'-(ethylenedioxy)bis(ethylamine) and 1.2 M DEDA (diethylene glycol diamine) in DMSO was prepared.

A rabbit Achilles tendon, previously stored at −70° C., was dissected from the remaining muscle, cleaned of fascia and muscle, and divided in half along its length.

One tendon piece was placed diagonally on a fused silica (UV transparent) glass slide and several drops of the mixture was placed in the center of the tendon piece. The other tendon piece was placed on top, forming an "X" shape with the mixture in between the two pieces at their intersection. Another identical slide was placed on top and light pressure was applied to the two slides.

The tendons and slides were then placed beneath a liquid light guide that delivered light from a filtered mercury-arc light source (320–500 nm, 2 W) and exposed for 500 sec (1,000 J).

After light exposure, the tendons were removed from the slide and placed on an illuminated grid beneath a CCD camera with a macro lens. An image of the overlapped (i.e. "welded") area was digitized and stored. Measurement of the overlapped area was made using standard computer software. It was observed that the tendon was welded together.

The welded tendon was then placed in a tensiometer to measure tensile strength. One tendon end was clamped and attached to a strain gauge, while the opposite end of the other tendon clamped to a block moved by a lead screw. When the tensiometer motor was activated, turning the lead screw, the force on the bonded tendon gradually increased. The force transduced by the strain gauge was digitized by a computer with an analog-to-digital converter and displayed as a Stress-Strain curve. Force was continuously increased until the bonded tendon pieces separated.

The maximum force tolerated by the bonded tendon before breaking was divided by the bonded area to calculate the Maximum Stress in Newtons/cm$^2$. It was found to be 31.7 N/cm$^2$.

Thus, there has been shown and described a product relating to a phototriggered composition which fulfills all the objects and advantages sought therefore. It is apparent to those skilled in the art, however, that many changes, variations, modifications, and other uses and applications for the composition are possible, and also such changes, variations, modifications, and other uses and applications which do not depart from the spirit and scope of the invention are deemed to be covered by the invention, which is limited only by the claims which follow.

What is claimed and desired to be secured by Letters Patent is as follows:

1. A method for crosslinking proteins comprising:
   (a) forming a hydrophilic, non-toxic photoactive composition;
   (b) applying said composition to a tissue with the tissue comprised of collagen, whereby the tissue wound is repaired; and,
   (c) irradiating such composition at a wavelength to form a reactive intermediate composition that forms covalent bonds with collagen protein, wherein the said intermediate is a ketoketene.

2. The method of claim 1 wherein said photoactive composition comprises a solution selected from the group consisting of buffered saline and DMSO.

3. The method of claim 1 wherein said intermediate composition forms a covalent bond with the collagen protein via the free amine of an amino acid of said protein.

4. The method of claim 3 wherein said amino acid is lysine.

5. The method of claim 1 wherein said wavelength is between 330 nm and 400 nm.

* * * * *